(12) United States Patent
Iori

(10) Patent No.: US 8,293,682 B2
(45) Date of Patent: Oct. 23, 2012

(54) GROWTH REGULATORS FOR GRAMINEOUS WEEDS

(75) Inventor: Shinichi Iori, Taito-ku (JP)

(73) Assignees: Rikengreen Co., Ltd., Tokyo (JP); Kumiai Chemical Industry Co., Ltd., Tokyo (JP)

(*) Notice: Subject to any disclaimer, the term of this patent is extended or adjusted under 35 U.S.C. 154(b) by 283 days.

(21) Appl. No.: 12/579,921

(22) Filed: Oct. 15, 2009

(65) Prior Publication Data

US 2010/0099567 A1 Apr. 22, 2010

(30) Foreign Application Priority Data

Oct. 20, 2008 (JP) ................................. 2008-269355

(51) Int. Cl.
*A01N 57/20* (2006.01)
*A01N 43/90* (2006.01)
*C07D 473/00* (2006.01)
*A01P 21/00* (2006.01)
*A01P 13/00* (2006.01)

(52) U.S. Cl. .................. 504/208; 544/277; 504/241

(58) Field of Classification Search .................. None
See application file for complete search history.

(56) References Cited

FOREIGN PATENT DOCUMENTS

| EP | 0155911 | * | 3/1985 |
|----|---------|---|--------|
| EP | 0 155 911 A1 | | 9/1985 |
| JP | 55-162706 | | 12/1980 |
| JP | 61-5080 | | 1/1986 |
| JP | 61-111626 | | 5/1986 |
| JP | 2-311477 | | 12/1990 |
| JP | 3-86803 | | 4/1991 |
| JP | 4-234801 | | 8/1992 |
| JP | 7-82113 | | 3/1995 |
| JP | 8-506107 | | 7/1996 |
| JP | 2000-86401 | | 3/2000 |
| JP | 2003-113008 | | 4/2003 |
| WO | WO 94/17062 | | 8/1994 |
| WO | WO 2010/047185 A1 | | 4/2010 |

OTHER PUBLICATIONS

McCullough, P. E.; Liu, H.; McCarty, L. Hortscience, 2005, 40(3), 836-838.*
Herzog, H.; Geisler, G. Z. Acker- and Pflanzenbau/J. Agronomy & Crop Science, 1976, 143, 134-147.*
H. Herzog, et al., "Der Einfluβ von Cytokinin-Applikationen auf die Bestockung und Organogenese der Ähre bei Sommerweizen", Z. Acker- und Pflanzenbau (J. Agronomy & Crop Science), vol. 143, 1976, pp. 134-147.
Noyaku Binran, Handbook of Agrochemicals, 8$^{th}$ Edition, 1995, 5 pages.
Fumitaka Tango, et al., "Growth Pattern of Seedlings of *Zoysia japonica* Steud and Their Responses to Plant Growth Regulators", Study of Lawn Grass, vol. 23, No. 2, 1995, pp. 5-11.
J. L. Eggens, et al., "Kentucky Bluegress and Annual Bluegrass Response to Ethephon", J. Amer. Soc. Hortic. Sci., vol. 110, No. 5. 1985, pp. 609-611.
Patrick E. McCullough, et al., "Response of Creeping Bentgrass to Nitrogen and Ethephon", HortScience, vol. 40, No. 3, 2005, pp. 836-838.

* cited by examiner

*Primary Examiner* — Johann Richter
*Assistant Examiner* — Erin Hirt
(74) *Attorney, Agent, or Firm* — Oblon, Spivak, McClelland, Maier & Neustadt, L.L.P.

(57) ABSTRACT

The invention provides a growth regulator for gramineous weeds, particularly those growing in turf, which comprises, as an active ingredient, cytokinin and/or an ethylene-producing substance in combination with cytokinin; and a method for regulating the growth of gramineous weeds with the relevant growth regulator more economically with ease.

20 Claims, No Drawings

GROWTH REGULATORS FOR GRAMINEOUS WEEDS

BACKGROUND OF THE INVENTION

1. Field of the Invention

The present invention relates to growth regulators for gramineous weeds and a method for regulating the growth of gramineous weeds using the same.

2. Description of the Related Art

Previously, Japanese lawn grasses have been used in various fields such as parks, gardens, playgrounds, golf courses, and the like. In Japanese lawn grasses, however, the growth is arrested during winter and the leaves turn yellow, and therefore in recent years cool temperate grasses which grow up through the winter have been used in a variety of fields.

In cultivation and maintenance of lawn grasses, it is inevitable that weeds invade the lawn.

These weeds sometimes disturb the growth of lawn grasses, spoil the beauty of lawn, and have an influence on a sporting event. For example, when gramineous weeds such as annual bluegrass (Poa annua L.) and southern crabgrass (Digitaria ciliaris Koel.), invade and colonize in the green field of a golf course, those weeds form the ears on the green; in particular, the white ears of annual bluegrass (Poa annua L.) would spoil the scenery and have an influence on putting in golf.

As for a conventional method for weeding in turf, clipping of lawn grasses with a lawn mower has been employed in order to prevent the growth of annual weeds. For example, in a bent grass green of a golf course, frequent clippings of weeds with a lawn mower wither and kill most of the annual weeds, thereby suppressing the growth of weeds to a large degree. Annual bluegrass (Poa annua L.) and southern crabgrass (Digitaria ciliaris Koel.), however, do not result in dying by clipping with a lawn mower. In addition, a large number of seeds produced by the ear emergence of Annual bluegrass (Poa annua L.) and southern crabgrass (Digitaria ciliaris Koel.) buds and colonizes, thereby growing to strong noxious weeds in a lawn field.

On the other hand, since annual bluegrass (Poa annua L.) strongly resists clipping with a lawnmower as mentioned above, it is said that if no appearance of ear is developed, the annual bluegrass per se could be utilized as a lawn grass of high quality.

In recent years, a large number of herbicides have been developed in order to control grass weeds in turf, and in Japanese lawn grasses, it is practically possible to control weeds only without chemical injury to lawn grasses using existing herbicides.

On the contrary, the existing herbicides are not sufficient in the herbicidal activity or sometimes cause chemical injury for cool temperate Western lawn grasses such as bent grass. This indicates that they are not necessarily satisfactory herbicides in the present circumstance.

Alternatively, there are also reports of a method to take care of the growth of lawn grasses without any herbicides by regulating the growth of lawn grasses or weeds using a plant hormone.

As for techniques for regulating the growth of lawn grasses, it has been reported that benzyladenine has an effect for accelerating the rooting of lawn grasses (Non-patent document 1), that benzyladenine has an effect for accelerating the growth of lawn grasses (Patent document 1), that ethephon (2-chloroethylphosphonic acid) promotes the extension of stolon and increase of the weight in lawn grasses (Non-patent document 2), and that gibberellins and cytokinins can be used for accelerating the growth of lawn grasses (Patent document 2). However, none of these documents describe any techniques for controlling weeds in turf.

As for a technique for controlling weeds, there is a method which involves accelerating the ear emergence of annual bluegrass (Poa annua L.) by application of gibberellin on lawn grasses of a golf course and mowing the ears which have grown taller than the lawn grasses (Patent document 3); in this method, however, there is a problem that the grown ears of annual bluegrass (Poa annua L.) have to be mowed by hand. In addition, it has been reported that annual bluegrass (Poa annua L.) growing among Kentucky bluegrass has slowed growth by treatment with ethephon (Non-patent document 3); and that ethephon inhibits the ear emergence of annual bluegrass (Poa annua L.) growing among bent grass (Non-patent document 4). These methods, however, have the disadvantage that a large quantity of ethephon has to be applied, that is, at a dose of 3.2 kg/hectare for the methods of Non-patent document 3, and 3.8-7.6 kg/hectare for Non-patent document 4. In addition, Non-patent document 4 describes that a large quantity of nitrogen fertilizer has to be applied in order to reduce chemical injury of bent grass.

As mentioned above, though several methods for controlling gramineous weeds such as annual bluegrass (Poa annua L.) growing in turf have been reported, none of them can control these weeds to a satisfactory extent or regulate their growth easily and economically.

Non-patent document 1: Noyaku Binran (Handbook of Agrochemicals), 8th edition, Nobunkyo, 1995

Non-patent document 2: Shibakusa Kenkyu (Study of Lawn Grass), vol. 23, no. 2, p. 5-11 (1995)

Non-patent document 3: J. Am. Soc. Hortic. Sci. (1985), 110(5), 609-611

Non-patent document 4: HortScience (2005), 40(3), 836-838

Patent document 1: JP-A-55-162706
Patent document 2: JP-A-7-82113
Patent document 3: JP-A-61-111626

SUMMARY OF THE INVENTION

A purpose of the present invention is to find out a growth regulator which has a property of regulating the growth of gramineous weeds, particularly those growing in turf, and to provide a method for regulating the growth of gramineous weeds with the growth regulator more economically with ease.

In order to solve the above problems, the present inventor worked assiduously to elucidate the inhibitory effect of a variety of plant hormones for gramineous weeds. As a result, it was found that in gramineous weeds, particularly in annual bluegrass (Poa annua L.) belonging to the genus Poa and southern crabgrass (Digitaria ciliaris Koel.) belonging to the genus Digitaria, the ear emergence of these gramineous weeds could be inhibited to increase the number of bud by treating them with a cytokinin or a mixture of cytokinin and ethylene-producing substance. In addition, it was also found that the treatment showed high safety to lawn grasses. Thus, the present invention was completed.

Namely, the present invention may be summarized as follows.

(1) A growth regulator for gramineous weeds, which comprises cytokinin as an active ingredient.

(2) A growth regulator for gramineous weeds as described in the above item (1), which further comprises an ethylene-producing substance.

(3) A growth regulator for gramineous weeds as described in the above item (1) or (2), wherein the cytokinin is benzyladenine.

(4) A growth regulator for gramineous weeds as described in any one of the above items (1) to (3), wherein the ethylene-producing substance is ethephon.

(5) A growth regulator for gramineous weeds as described in any one of the above items (1) to (4), wherein the gramineous weeds are those belonging to the genus *Poa* or *Digitaria*.

(6) A growth regulator for gramineous weeds as described in any one of the above items (1) to (5), wherein the gramineous weed is annual bluegrass (*Poa annua* L.) or southern crabgrass (*Digitaria ciliaris* Koel.).

(7) A kit for regulating the growth of gramineous weeds, which comprises the first agent containing cytokinin and the second agent containing an ethylene-producing substance.

(8) A kit for regulating the growth of gramineous weeds as described in the above item (7), wherein the cytokinin is benzyladenine.

(9) A kit for regulating the growth of gramineous weeds as described in the above item (7) or (8), wherein the ethylene-producing substance is ethephon.

(10) A kit for regulating the growth of gramineous weeds as described in any one of the above items (7) to (9), wherein the gramineous weeds are those belonging to the genus *Poa* or *Digitaria*.

(11) A kit for regulating the growth of gramineous weeds as described in any one of the above items (7) to (9), wherein the gramineous weed is annual bluegrass (*Poa annua* L.) or southern crabgrass (*Digitaria ciliaris* Koel.).

(12) A method for regulating the growth of gramineous weeds, which comprises treating gramineous weeds with a plant growth regulator as described in any one of the above items (1) to (6).

(13) A method for regulating the growth of gramineous weeds as described in the above item (12), which comprises regulating the growth of gramineous weeds growing in turf.

(14) A method for regulating the growth of gramineous weeds using a kit for regulating the growth of gramineous weeds as described in any one of the above items (7) to (9), which comprises applying the first agent containing cytokinin and the second agent containing an ethylene-producing substance at the same time or at different times.

(15) A method for regulating the growth of gramineous weeds as described in the above item (14), which comprises regulating the growth of gramineous weeds growing in turf.

EFFECT OF THE INVENTION

By treating gramineous weeds with a growth regulator for gramineous weeds or a kit for regulating the growth of gramineous weeds according to the present invention, it is possible to inhibit the ear emergence and increase the number of bud. This treatment can be performed with high safety for lawn grasses.

Thus, the growth regulator and growth regulating kit for gramineous weeds according to the present invention are particularly suitable for treatment of gramineous weeds growing in turf, and it is possible to produce turf of high quality through the treatment.

DESCRIPTION OF THE PREFERRED EMBODIMENTS

The cytokinins used as an active ingredient in the growth regulator for gramineous weeds of the present invention (hereinafter, simply referred to as "regulator of the invention") include, but are not particularly limited to, zeatin (2-methyl-4-(7H-purinyl-6-amino)-2-buten-1-ol), kinetin (6-furfurylamino-purine), benzyladenine (6-benzylaminopurine), and forchlorfenuron (1-(2-chloro-4-pyridyl)-3-phenylurea); benzyladenine is particularly preferred.

The content of the above cytokinin in the regulator of the invention may preferably be chosen depending on the formulation. In a case of dust formulation, the content may properly be set in the range of 0.01-10% by weight (hereinafter, simply referred to as "%"), preferably 0.05-5%. When emulsifiable concentrate, wettable powder, oil miscible liquid, water dispersible granule or flowable formulation is employed, the content may properly be chosen from the range of 1-50%, preferably 5-30%.

In the regulator of the invention, the above cytokinin may be contained alone as active ingredient, or alternatively an ethylene-producing substance may be added as an additional active ingredient; this is preferred in view of increasing the effectiveness. There is no particular limitation in the ethylene-producing substance as far as it releases ethylene or acts as an ethylene precursor. Such a substance includes, for example, ethephon (2-chloroethylphosphonic acid) and 1-amino-cyclopropane-1-carboxylic acid (ACC); and ethephon is particularly preferred.

The content of ethylene-producing substance used in combination with a cytokinin is selected from the range of 1.25-310 times, preferably 2.5-100 times, more preferably 6-40 times, to cytokinin by mass. The ratio of the combination may properly be variable depending on the growing period of weeds or lawn grasses.

The regulator of the invention, if required, may contain at least one additive such as a carrier including solid carrier and liquid carrier, surfactant, binder or sticking agent, thickener, coloring agent, anti-freezing agent, anti-caking agent, disintegrator, decomposition inhibitor, and antiseptics, in addition to cytokinin alone or in combination with an ethylene-producing substance. These additives may be used alone or in combination of two or more thereof.

The solid carrier added where necessary includes, for example, naturally occurring mineral matters such as quartz, clay, kaolinite, pyrophyllite, sericite, talc, bentonite, Japanese acid clay, attapulgite, zeolite, and diatom earth; inorganic salts such as calcium carbonate, ammonium sulfate, sodium sulfate, and potassium chloride; organic solid carrier such as synthetic silicic acid, synthetic silicate, starch, cellulose, and plant powder; plastic carrier such as polyethylene, polypropylene, and polyvinyliden chloride. These may be used alone or in combination of two or more thereof.

The liquid carrier includes, for example, alcohols roughly classified into monohydric alcohols such as methanol, ethanol, propanol, isopropanol, and butanol, and polyhydric alcohols such as ethylene glycol, diethylene glycol, propylene glycol, hexylene glycol, polyethylene glycol, polypropylene glycol, and glycerin; polyhydric alcohol derivatives such as propylene glycol ethers; ketones such as acetone, methyl ethyl ketone, methyl isobutyl ketone, diisobutyl ketone, cyclohexanone, and isophorone; ethers such as ethyl ether, dioxane, cellosolve, dipropyl ether, and tetrahydrofuran; aliphatic hydrocarbons such as normal paraffin, naphthene, isoparaffin, kerosene, and mineral oil; aromatic hydrocarbons such as benzene, toluene, xylene, solvent naphtha, and alkylnaphthalene; halogenated hydrocarbons such as dichloroethane, chloroform, and carbon tetrachloride; esters such as ethyl acetate, diisopropyl phthalate, dibutyl phthalate, dioctyl phthalate, and dimethyl adipate; lactones such as γ-butyrolactone; amides such as dimethylformamide, diethyl-formamide, dimethylacetamide, and N-alkylpyrrolidine; nitriles such as acetonitrile; sulfur-containing compounds such as dimethylsulfoxide; plant oils such as soybean oil, rape seed oil, cotton seed oil, and castor oil; and water. These may be used alone or in combination of two or more thereof.

The surfactant includes, but is not limited particularly to, nonionic surfactants such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkylphenyl ether, polyoxyethylene dialkylphenyl ether, polyoxyethylene alkylphenyl ether formalin condensate, polyoxyethylene polyoxypropylene block polymer, alkyl polyoxyethylene polypropylene block polymer ether, polyoxyethylene alkylamine, polyoxyethylene fatty acid amide, polyoxyethylene fatty acid bisphenyl ether, polyalkylene benzylphenyl ether, polyoxyalkylene styrylphenyl ether, acetylenediol, polyoxyalkylene-added acetylenediol, polyoxyethylene ether-type silicone, ester-type silicone, fluorine-type surfactant, polyoxyethylene castor oil, and polyoxyethylene hardened castor oil; anionic surfactants such as alkyl sulfate, polyoxyethylene alkyl ether sulfate, polyoxyethylene alkylphenyl ether sulfate, polyoxyethylene styrylphenyl ether sulfate, alkylbenzenesulfonate, ligninsulfonate, alkylsulfosuccinate, naphthalenesulfonate, alkylnaphthalenesulfonate, naphthalenesulfonic acid formalin condensate salt, alkylnaphthalenesulfonic acid formalin condensate salt, fatty acid salt, polycarboxylate, N-methylfatty acid sarcosinate, resin acid salt, polyoxyethylene alkyl ether phosphate, and polyoxyethylene alkylphenyl ether phosphate; cationic surfactants including alkylamine salts such as laurylamine hydrochloride, stearylamine hydrochloride, oleylamine hydrochloride, stearylamine acetate, stearylaminopropylamine acetate, alkyltrimethylammonium chloride and alkyldimethylbenzalkonium chloride; and ampholytic surfactants of amino acid type or betaine type. These surfactants may be used alone or in combination of two or more thereof.

The binders and sticking agents are exemplified by carboxymethylcellulose or salts thereof, dextrin, water-soluble starch, xanthan gum, guar gum, cane sugar, polyvinylpyrrolidone, gum arabic, polyvinyl alcohol, polyvinyl acetate, sodium polyacrylate, polyethylene glycol having an average molecular weight of 6000-20000, polyethylene oxide having an average molecular weight of 100,000-5,000,000, and naturally occurring phospholipids (e.g., cephalinic acid, lecithin).

The thickener includes, for example, water-soluble polymers such as xanthan gum, guar gum, carboxymethylcellulose, polyvinylpyrrolidone, carboxyvinyl polymer, acrylic polymer, starch derivatives, and polysaccharides; and inorganic fine powder such as highly pure bentonite and white carbon.

The coloring agent includes, for example, inorganic pigments such as iron oxide, titanium oxide, and prussian blue; and organic dyestuffs such as alizarin dye, azo dye, and metallic phthalocyanine pigment.

The anti-freezing agent includes, for example, polyhydric alcohols such as ethylene glycol, diethylene glycol, propylene glycol, and glycerin.

The anti-caking agent includes, for example, polysaccharides such as starch, alginic acid, mannose, and galactose, polyvinylpyrrolidone, white carbon, ester gum, and petroleum resin.

The disintegrator includes, for example, sodium tripolyphosphate, sodium hexametaphosphate, metallic stearate, cellulose powder, dextrin, methacrylate copolymer, polyvinylpyrrolidone, polyaminocarboxylic acid chelate compound, sulfonated styrene/isobutylene/maleic acid anhydride copolymer, and starch polyacrylonitrile graft copolymer.

The decomposition inhibitor includes, for example, drying agents such as zeolite, quick lime, and magnesium oxide; anti-oxidants of phenol-type, amine-type, sulfur-type, and phosphate-type; and ultra-violet absorbents of salicylic acid type and benzophenone type.

The antiseptics include, for example, potassium sorbate, and 1,2-benzthiazolin-3-one.

When the carrier is contained in the regulator of the invention, the content is usually 1-95%, preferably 5-85%, more preferably 20-75% based on mass of the formulation. For the surfactant, the content is usually 0.1-30%, preferably 0.2-20%, more preferably 0.5-10%. For the other additives, it is in the range of 0.1-30%, preferably 0.3-10%, more preferably 0.5-5%.

In addition, the regulator of the invention may comprise at least one of other agrochemicals such as herbicides, insecticides, bactericides, and plant growth regulating agents, as well as safeners, fertilizers, soil-penetrating agents, or the like.

The known herbicidal compounds and plant growth regulating agents which are miscible with the regulator of the invention include, for example, asulam, pyrazosulfuron-ethyl, mecoprop-P, mecoprop-P potassium, halosulfuron-methyl, endothal-disodium, ethoxysulfuron, metsulfuron-methyl, triclopyr-triethylammonium, flazasulfuron, imazosulfuron, carfentrazone-ethyl, cyclosulfamuron, iodosulfuron-methyl-sodium salt, rimsulfuron, MDBA (dicamba), MCPA-isopropylamine salt, benfuresate, florasulam, trifloxysulfuron-sodium salt, fluazifop-P, pendimethalin, pyributicarb, propyzamide, ACN (quinoclamine), napropamide, prodiamine, DCBN (chlorthiamid), oryzalin, CAT (simazine), butamifos, dithiopyr, siduron, cafenstrole, bethrodine (benfluralin), alachlor, oxadiargyl, oxaziclomefone, orbencarb, metamifop, flupoxame, isoxaben, pyraflufen-ethyl, etobenzanid, pyrimisulfan, cumyluron, lenacil, indole butyric acid, ethychlozate, cloxyfonac, dichlorprop, 1-naphthylacetamide, 4-CPA, forchlorfenuron, gibberellin acid, maleic hydrazide, inabenfide, uniconazole-P, chlormequat, paclobutrazol, flurprimidol, prohexadione-calcium salt, trinexapac-ethyl, bispyribac-sodium salt, daminozide, mefluidide, oxyethylene docosanol, paraffin, wax, chlorella extracts, extract from 12 plant-leaves, and extract from the mycelia of shiitake mushroom.

The known bactericidal compounds include, for example, acibenzolar-S-methyl, azoxystrobin, ametocradin, amisulbrom, aldimorph, isotianil, isopyrazam, isoprothiolane, ipconazole, iprodione, iprovalicarb, iprobenfos, imazalil, iminoctadine-albesilate salt, iminoctadine-triacetate salt, imibenconazole, edifenphos, ethaboxam, ethoxyquin, echlomezole (etridiazole), enestroburin, epoxiconazole, oxadixyl, oxazinylazole, oxycarboxin, oxytetracycline, oxpoconazole fumarate, oxolinic acid, octhilinone, ofurace, orysastrobin, o-phenylphenol, kasugamycin, captafol, carpropamid, carbendazim, carboxin, quinoxyfen, chinomethionat, captan, quintozene, guazatine, kresoxim-methyl, TPN (chlorothalonil), chloroneb, cyazofamid, diethofencarb, diclocymet, dichlofluanid, diclomezine, dicloran, dithianon, diniconazole, zineb, dinocap, diphenyl, diphenylamine, difenoconazole, difenzoquat methyl sulfate, cyflufenamid, diflumetorim, cyproconazole, cyprodinil, simeconazole, dimethomorph, cymoxanil, dimoxystrobin, ziram, silthiofam, streptomycin, spiroxamine, zoxamide, dazomet, tiadinil, thiabendazole, thiophanate-methyl, thifluzamide, thiram, tecnazene, tecloftalam, tetraconazole, debacarb, tebuconazole, tebufloquin, dodine, dodemorph, triadimenol, triadimefon, triazoxide, tricyclazole, triticonazole, tridemorph, triflumizole, trifloxystrobin, triforine, tolylfluanid, tolclofos-methyl, tolnifanide, nabam, nitrothal-isopropyl, nuarimol, validamycin, valifenalate, bixafen, picoxystrobin, bitertanol, piperalin, hydroxyisoxazole (hymexazol), pyraclostrobin, pyrazophos, pyrifenox, pyributicarb, pyribencarb, pyrimethanil, pyrametostrobin, pyraoxystrobin, pyroquilon, vinclozolin, ferbam, famoxadone, fenamidone, fenarimol, fenoxanil, ferimzone, fenbuconazole, fenfuram, fenpropidin, fenpropimorph, fenhexamid, folpet, phthalide, bupirimate, fuberidazole, furametpyr, furalaxyl, fluazinam, fluoxastrobin, fluopicolide, fluopyram, fluoroimide, fluquinconazole, fludioxonil, flusilazole, flusulfamide, flutolanil, flutriafol, flumorph, proquinazid, prochloraz, procymidone, prothioconazole, bronopol, propamocarb-hydrochloride, propiconazole, propineb, probenazole, bromuconazole, hexaconazole, benalaxyl, benalaxyl-M, benomyl, pefurazoate, penconazole, pencycuron, benthiavalicarb-isopropyl, penthiopyrad, boscalid, fosetyl-alminium, polyoxin, polycarbamate, mancozeb, mandipropamid, maneb, myclobutanil, mildiomycin, methasulfocarb, metam, metalaxyl, metalaxyl-M, metconazole, metominostrobin, metrafenone, mepanipyrim, mepronil, copper sulfate, copper hydroxide, cuprous oxide, copper oxychloride, oxyquinoline sufate, copper (nonylphenyl)sulphonate, 8-hydroxyquinoline copper (oxine-copper), mancopper, silver, sulfur, potassium bicarbonate, and Bordeaux mixture.

The known insecticidal and nematicidal compounds include, for example, 1,3-dichloropropene, DCIP, DNOC, EPN, acrinathrin, azamethiphos, azinphos-ethyl, azinphos-methyl, acequinocyl, acetamiprid, acetoprol, acephate, azocyclotin, abamectin, amitraz, alanycarb, aldicarb, alpha-cypermethrin, allethrin, isoxathion, isofenphos-methyl, isocarbophos, MIPC (isoprocarb), imicyafos, imidacloprid, imiprothrin, indoxacarb, esfenvalerate, ethiofencarb, ethion, ethiprole, etoxazole, etofenprox, ethoprophos, emamectin, endosulfan, empenthrin, oxamyl, oxydemeton-methyl, omethoate, cadusafos, karanjin, cartap, carbaryl, carbosulfan, carbofuran, gamma-cyhalothrin, xylylcarb, quinalphos, kinoprene, chinomethionat, coumaphos, clothianidin, clofentezine, chromafenozide, chlorantraniliprole, chlorethoxyfos, chlordane, chloropicrin, chlorpyrifos, chlorpyrifos-methyl, chlorfenapyr, chlorfenvinphos, chlorfluazuron, chlormephos, cyazypyr, cyanophos, diafenthiuron, dienochlor, cyenopyrafen, dicrotophos, dichlofenthion, cycloprothrin, dichlorvos, dicofol, dicyclanil, disulfoton, dinotefuran, dinobuton, cyhalothrin, cyphenothrin, cyfluthrin, diflubenzuron, cyflumetofen, diflovidazin, cyhexatin, cypermethrin, dimethylvinphos, dimethoate, silafluofen, cyromazine, spinetoram, spinosad, spirodiclofen, spirotetramat, spiromesifen, sulcofuron-sodium, sulfluramid, sulfotep, sulfoxaflor, zeta-cypermethrin, diazinon, tau-fluvalinate, thiacloprid, thiamethoxam, thiodicarb, thiocyclam, thiosultap, thiofanox, thiometon, tetrachlorvinphos, tetradifon, tetramethrin, tebupirimfos, tebufenozide, tebufenpyrad, tefluthrin, teflubenzuron, demeton-S-methyl, temephos, deltamethrin, terbufos, tralomethrin, transfluthrin, triazamate, triazophos, DEP (trichlorfon), triflumuron, trimethacarb, tolfenpyrad, naled, nicotine, nitenpyram, novaluron, noviflumuron, hydroprene, vamidothion, parathion, parathion-methyl, halfenprox, halofenozide, bioallethrin, bioresmethrin, bistrifluron, hydramethylnon, bifenazate, bifenthrin, pymetrozine, pyraclofos, pyridaphenthion, pyridaben, pyridalyl, pyrifluquinazon, pyriproxyfen, pirimicarb, pyrimidifen, pirimiphos-methyl, famphur, fipronil, fenazaquin, fenamiphos, MEP (fenitrothion), fenoxycarb, fenothiocarb, phenothrin, fenobucarb, fenthion, phenthoate, fenvalerate, fenpyroximate, fenbutatin oxide, fenpropathrin, butocarboxim, butoxycarboxim, buprofezin, furathiocarb, prallethrin, fluacrypyrim, flucycloxuron, flucythrinate, flusulfamide, fluvalinate, flupyrazofos, flufenerim, flufenoxuron, flubendiamide, flumethrin, flurimfen, prothiofos, flonicamid, propaphos, propargite, profenofos, propetamphos, propoxur, bromopropylate, beta-cyfluthrin, hexythiazox, hexaflumuron, heptenophos, permethrin, bensultap, benzoximate, bendiocarb, benfuracarb, phoxim, phosalone, fosthiazate, phosphamidon, phosmet, formetanate, phorate, malathion, milbemectin, mecarbam, mesulfenfos, methomyl, metaflumizon, methamidophos, metham, methiocarb, methidathion, methyl isothiocyanate, methoxychlor, methoxyfenozide, methothrin, metofluthrin, methoprene, mevinphos, monocrotophos, lambda-cyhalothrin, lufenuron, resmethrin, lepimectin, rotenone, and B.T. (*Bacillus thuringiensis*).

In this connection, a commercially available preparation respectively containing the above agrochemicals, safener, fertilizer, soil-penetrating agent, and the like may be used concurrently, instead of mixing, with the regulator of the invention.

The regulator of the invention may be formulated into an optional formulation such as soluble concentrate, emulsifiable concentrate, wettable powder, dust, oil miscible liquid, water dispersible granule, flowable formulation, and granule according to a conventional manner.

Thus obtained regulator of the invention is applied to regulate the growth of gramineous weeds, preferably weeds of the genus *Poa* such as Ichigotsunagi (*Poa sphondylodes*), Kentucky bluegrass (*Poa pratensis* L.), and annual bluegrass (*Poa annua* L.), and weeds of the genus *Digitaria* such as southern crabgrass (*Digitaria ciliaris* Koel.); more preferably annual bluegrass (*Poa annua* L.) or southern crabgrass (*Digitaria ciliaris* Koel.). Further, by applying the regulator of the invention to turf, the growth of gramineous weeds are regulated without affecting lawn grasses. The regulator of the invention may be directly applied to turf in such a form as the above formulations, and in such a case, a dust or granular formulation is preferably used. In general, the regulator of the invention is diluted in water before use. The diluted agent is scattered with a sprayer or atomizer at the place where the active ingredient of regulator of the invention can penetrate into plants, for example, on the leaves and stems of lawn grasses or gramineous weeds or over the soil.

In the treatment of gramineous weeds by the regulator of the invention, when cytokinin is used as a single active ingredient, it maybe applied at a dose of 1-32 mg, preferably 2-24 mg, more preferably 4-16 mg for 1 $m^2$ of application area. The regulator of the invention which is diluted with an appropriate concentration may preferably scattered, though it may be used directly.

When cytokinin is used in combination with an ethylene-producing substance, the regulator may be applied at a dose of 0.5-16 mg as cytokinin and 20-320 mg as the ethylene-producing substance, preferably 1-16 mg and 40-240 mg, and more preferably 2-12 mg and 80-160 mg, respectively, for 1 $m^2$ of application area.

The regulator of the invention may be applied at any time throughout the year for treatment of gramineous weeds. However, since the growth-regulating action for gramineous weeds works slowly, it is preferred to apply the regulator just before the ear emergence of gramineous weeds. The regulator of the invention, when cytokinin is applied alone, may be applied every 5-60 days, preferably every 10-30 days, more preferably every 15-20 days. When cytokinin is used in combination with an ethylene-producing substance, the regulator may be applied every 10-70 days, preferably every 20-50 days, more preferably every 25-35 days.

The species of lawn grasses to which the regulator of the invention can be applied are not particularly limited, and specifically include Japanese lawn grasses such as Manilagrass (*Zoysia matrella*), Mascarengrass (*Zoysia tenuifolia*), Kinushiba, and Japanese lawngrass (*Zoysia japonica*); summer western lawn grasses such as Bermuda grass and Bahia grass; and cool temperature grasses such as bent grass, ryegrass, blue grass and fescue. The regulator of the invention may also be applied to lawn grasses transformed by gene engineering, which show resistance against herbicides, insect pest or disease injury, which show drought resistance, and which show salt tolerance.

In this connection, when cytokinin is used in combination with an ethylene-producing substance as mentioned above, a kit for regulating the growth of gramineous weeds, which contains the first agent containing cytokinin and the second agent containing an ethylene-producing substance, may be utilized as substitute for the above mixed formulation. Herein, a commercially available cytokinin preparation and a commercially available ethylene-producing preparation may be used as the first agent containing cytokinin and the second agent containing an ethylene-producing substance, respectively.

When gramineous weeds are treated with this kit, the first agent containing cytokinin may be used at the same time or at a different time point with the second agent containing an ethylene-producing substance. The term "different time point" used in this invention means that the respective agents are applied alternately at appropriate intervals. Actually, an appropriate interval is of 1-30 days, preferably 1-20 days, more preferably 1-10 days.

EXAMPLES

The process for preparing the formulations of the invention will be explained specifically by the following representative examples of formulations. The compounds, additives, and their kind or compounding ratio may be varied in a wide range without any limitation to them. In the following explanation, the term "part" means part by mass.

Formulation 1
Soluble Concentrate

In a stirring vessel, 44.0 parts of water, 15.0 parts of propylene glycol methyl ether, 20.0 parts of dimethylsulfoxide and 10.0 parts of polyoxyethylene sorbitan monolaurate were mixed. 10.0 parts of ethephon and 1.0 part of benzyladenine were added to the mixture and mixed until completely dissolved, thereby forming a homogeneous soluble concentrate. If the respective components were changed, similar soluble concentrates could be prepared.

Formulation 2
Wettable Powder

In a mixer, 1.0 part of benzyladenine, 10.0 parts of ethephon, 5.0 parts of sodium ligninsulfonate, 0.5 parts of sodium dioctylsulfosuccinate, 5.0 parts of white carbon (Carplex #80; made by Shionogi & Co.) and 78.5 parts of mineral clays (Showa Fine Clay; made by Showa Kogyo) were mixed homogeneously. The resulting mixture was ground with an impact grinder and further mixed with a mixer to obtain a homogeneous wettable powder. If the respective components were changed, similar wettable powders could be prepared.

Formulation 3
Emulsifiable Concentrate

In a mixer, 44.0 parts of alkylnaphthalene (Solvesso 200; Exxon Chemical), 25.0 parts of N-methyl-2-pyrrolidone, 15.0 parts of polyoxyethylene tristyrene-phenyl ether and 5.0 parts of calcium decylbenzenesulfonate were mixed under stirring. 10.0 parts of ethephon and 1.0 part of benzyladenine were added to the mixture and mixed until completely dissolved, thereby forming a homogeneous emulsion. If the respective components were changed, similar emulsifiable concentrates could be prepared.

The following representative Test Examples will explain specifically the test methods employed.

Test Example 1

At the initial stage of the ear emergence of annual bluegrass (*Poa annua* L.) grown in a poly-cup of 11 cm×11 cm, benzyladenine (Beanine for painting; made by Rikengreen; containing 1% benzyladenine) and ethephon (Ethrel 10 soluble concentrate; Nissan Chemical Industries; containing 10% ethephon) respectively as a single active ingredient or a mixture of them were diluted in a predetermined amount of water and applied by atomization so as to be a dose as indicated in Table. The application was carried out using 100 mL/m² of the solution to which a spreader (Riken Sprayzer (registered trade mark); made by Rikengreen) was added so as to be ¹/₁,₀₀₀ fold. Inspection was made on Days 21, 32 and 45 after treatment with the agents to count the number of ear emergence in the cup. After completion of each inspection, clipping was performed. Tables 1-3 show the results.

TABLE 1

| 21 Days after Application | | Dose of Benzyladenine (mg a.i./m²) | | | | | |
|---|---|---|---|---|---|---|---|
| | | 0 | 2 | 4 | 8 | 12 | 16 |
| Dose of Ethephon (mg a.i./m²) | 0 | 57 | 39 | 26 | 36 | 16 | 11 |
| | 40 | 43 | 17 | 4 | 2 | 3 | 1 |
| | 80 | 47 | 15 | 1 | 3 | 2 | 2 |
| | 160 | 28 | 15 | 1 | 3 | 2 | 3 |
| | 240 | 29 | 16 | 7 | 2 | 2 | 1 |
| | 320 | 19 | 13 | 6 | 5 | 4 | 1 |

TABLE 2

| 32 Days after Application | | Dose of Benzyladenine (mg a.i./m²) | | | | | |
|---|---|---|---|---|---|---|---|
| | | 0 | 2 | 4 | 8 | 12 | 16 |
| Dose of Ethephon (mg a.i./m²) | 0 | 61 | 50 | 34 | 10 | 9 | 6 |
| | 40 | 38 | 25 | 1 | 0 | 0 | 0 |
| | 80 | 41 | 16 | 0 | 0 | 0 | 0 |
| | 160 | 32 | 5 | 0 | 0 | 0 | 0 |
| | 240 | 19 | 4 | 0 | 0 | 0 | 0 |
| | 320 | 15 | 1 | 0 | 0 | 0 | 0 |

TABLE 3

| 45 Days after Application | | Dose of Benzyladenine (mg a.i./m²) | | | | | |
|---|---|---|---|---|---|---|---|
| | | 0 | 2 | 4 | 8 | 12 | 16 |
| Dose of Ethephon (mg a.i./m²) | 0 | 63 | 71 | 71 | 67 | 55 | 45 |
| | 40 | 54 | 56 | 43 | 36 | 16 | 26 |
| | 80 | 51 | 31 | 42 | 25 | 20 | 29 |
| | 160 | 38 | 49 | 46 | 19 | 18 | 18 |
| | 240 | 39 | 44 | 36 | 11 | 7 | 5 |
| | 320 | 36 | 35 | 35 | 7 | 6 | 2 |

The above test results indicate that the application of benzyladenine was effective in inhibiting the ear emergence of annual bluegrass (*Poa annua* L.). The treatment with a mixed preparation of benzyladenine and ethephon was shown to be more effective.

Test Example 2

At the initial stage of the ear emergence of annual bluegrass (*Poa annua* L.) grown in a poly-cup of 11 cm×11 cm, benzyladenine (Beanine for painting; made by Rikengreen; containing 1% benzyladenine) and/or ethephon (Ethrel 10 soluble concentrate; Nissan Chemical Industries; containing 10% ethephon) were diluted in a predetermined amount of water, and a spreader (Riken Sprayzer (registered trade mark); made by Rikengreen) was added so as to be ¹⁄₁,₀₀₀-fold concentration; the respectively diluted solutions were applied by atomization at a dose and intervals as indicated in Table (scattered solution: 200 mL/m$^2$), and the number of emerged ears of annual bluegrass (*Poa annua* L.) in the cup was counted through time. The test was carried out serially. Table 4 shows the results. The symbol "●" in Table indicates the treatment with benzyladenine, "○" the treatment with ethephon, and "–" untreated. Dose means the amount at a single application.

TABLE 4

| Active ingredient | Application | | | | Count of ear emergence | |
|---|---|---|---|---|---|---|
| (Dose mg a.i./m$^2$) | Day 0 | Day 6 | Day 10 | Day 12 | Day 25 | Day 33 |
| Benzyladenine (0.67) | ● | ● | — | ● | 37 | 50 |
| | — | ● | — | ● | 34 | 24 |
| | — | — | — | ● | 37 | 28 |
| Benzyladenine (2) | ● | ● | — | ● | 20 | 26 |
| | — | ● | — | ● | 14 | 15 |
| | — | — | — | ● | 22 | 23 |
| Benzyladenine (0.67) + Ethephon (40) | ● | ● | ○ | ● | 22 | 19 |
| | — | ● | ○ | ● | 20 | 11 |
| | — | — | ○ | ● | 21 | 27 |
| Benzyladenine (2) + Ethephon (40) | ● | ● | ○ | ● | 7 | 2 |
| | — | ● | ○ | ● | 6 | 1 |
| | — | — | ○ | ● | 17 | 17 |
| Ethephon (40) | — | — | ○ | — | 35 | 27 |
| No treatment | — | — | — | — | 41 | 38 |

The above test results indicate that the alternate application of benzyladenine and ethephon was highly effective.

Test Example 3

At the initial stage of the ear emergence of annual bluegrass (*Poa annua* L.) grown in a poly-cup of 11 cm×11 cm, benzyladenine (Beanine for painting; made by Rikengreen; containing 1% benzyladenine) and ethephon (Ethrel 10 soluble concentrate; Nissan Chemical Industries; containing 10% ethephon) were diluted in a predetermined amount of water, and a spreader (Riken Sprayzer (registered trade mark); made by Rikengreen) was added so as to be ¹⁄₁,₀₀₀-fold concentration; the respectively diluted solutions were applied by atomization at a dose as indicated in Table (scattered solution: 200 mL/m$^2$), and after a lapse of 29 days, the 2nd application was carried out. Then, the number of emerged ears of annual bluegrass (*Poa annua* L.) in the cup was counted. Further, the number of leaves [Leaf] of annual bluegrass (*Poa annua* L.) was counted within the area of 6 cm×6 cm in the cup. The test was carried out serially. Table 5 shows the results. Dose means the amount at a single application.

TABLE 5

| Benzyladenine + Ethephon | Day 23 | Day 46 | | Day 53 |
|---|---|---|---|---|
| Dose (mg a.i./m$^2$) | Ear | Ear | [Leaf] | Ear |
| 0 + 20 | 30 | 34 | [90] | 34 |
| 0 + 40 | 23 | 27 | [88] | 30 |
| 0 + 80 | 13 | 29 | [79] | 41 |
| 2 + 0 | 12 | 54 | [105] | 43 |
| 2 + 20 | 1 | 4 | [148] | 25 |
| 2 + 40 | 3 | 4 | [138] | 15 |
| 2 + 80 | 2 | 2 | [135] | 3 |
| 4 + 0 | 2 | 55 | [108] | 48 |
| 4 + 20 | 0 | 2 | [132] | 8 |
| 4 + 40 | 0 | 2 | [145] | 13 |
| 4 + 80 | 0 | 2 | [150] | 12 |
| No treatment zone | 41 | 76 | [61] | 47 |

The above test results indicate that the treatment with benzyladenine alone or with the combination of benzyladenine and ethephon not only strongly inhibits the ear emergence, but also increases the number of leaves (bud number) of annual bluegrass (*Poa annua* L.) with the formation of deep green leaves.

Test Example 4

In a bent green turf where annual bluegrasses (*Poa annua* L.) were grown, a test zone of 1 m×1 m was provided. Benzyladenine (Beanine for painting; made by Rikengreen; containing 1% benzyladenine) and ethephon (Ethrel 10 soluble concentrate; Nissan Chemical Industries; containing 10% ethephon) were diluted in a predetermined amount of water, and a spreader (Riken Sprayzer (registered trade mark); made by Rikengreen) was added so as to be ¹⁄₁,₀₀₀-fold concentration. The respectively diluted solutions were applied to each test zone at the first application (Day 0) at a dose as indicated in Table, and after a lapse of 30 days the second application was carried out. The amount of solution scattered was 100 mL/m$^2$ both in the first and second applications. The number of ear emergence of annual bluegrass (*Poa annua* L.) within the area of 10×10 cm was counted at regular intervals at 3 spots per zone. Table 6 shows the results as the mean values of the emerged ear number. Dose means the amount at a single application.

TABLE 6

| Dose (mg a.i./m²) | | Day 22 | Day 41 | Day 61 |
|---|---|---|---|---|
| Ethephon | Benzyladenine | Ear | Ear | Ear |
| 0 | 0 | 96.7 | 160.7 | 147.3 |
| 80 | 0 | 53.7 | 57.3 | 68.7 |
| 160 | 0 | 25.0 | 24.3 | 59.0 |
| 0 | 4 | 62.3 | 150.3 | 107.0 |
| 80 | 4 | 20.0 | 19.7 | 31.7 |
| 160 | 4 | 14.7 | 6.0 | 14.3 |
| 0 | 8 | 34.3 | 59.7 | 53.0 |
| 80 | 8 | 17.3 | 8.3 | 13.7 |
| 160 | 8 | 2.3 | 1.3 | 4.3 |
| 0 | 12 | 27.0 | 32.7 | 41.0 |
| 80 | 12 | 5.3 | 2.3 | 8.7 |
| 160 | 12 | 1.0 | 0.7 | 3.3 |

TABLE 7

| Index | Inhibitory effect for ear emergence |
|---|---|
| 0 | 0% or more-less than 10% |
| 1 | 10% or more-less than 20% |
| 2 | 20% or more-less than 30% |
| 3 | 30% or more-less than 40% |
| 4 | 40% or more-less than 50% |
| 5 | 50% or more-less than 60% |
| 6 | 60% or more-less than 70% |
| 7 | 70% or more-less than 80% |
| 8 | 80% or more-less than 90% |
| 9 | 90% or more-less than 100% |
| 10 | 100% |

TABLE 8

| Test agent | Dose (mg a.i./m²) | Application | | Evaluation | | | |
|---|---|---|---|---|---|---|---|
| | | Day 0 | Day 17 | Day 18 | Day 26 | Day 33 | Day 41 |
| Benzyladenine | 2.5 | ● | — | 0 | 0 | 0 | 0 |
| | | ● | ● | | 1 | 3 | 1 |
| | 5 | ● | — | 0 | 0 | 1 | 2 |
| | | ● | ● | | 2 | 3 | 5 |
| | 10 | ● | — | 2 | 2 | 5 | 2 |
| | | ● | ● | | 6 | 7 | 6 |
| | 15 | ● | — | 10 | 9 | 7 | 4 |
| | | ● | ● | | 10 | 8 | 8 |
| Benzyladenine + Ethephon | 2.5 + 50 | ● | — | 0 | 0 | 1 | 2 |
| | | ● | ● | | 4 | 6 | 3 |
| | 5 + 50 | ● | — | 3 | 5 | 5 | 3 |
| | | ● | ● | | 8 | 7 | 4 |
| | 10 + 50 | ● | — | 6 | 7 | 6 | 5 |
| | | ● | ● | | 9 | 9 | 7 |
| Ethephon | 50 | ● | — | 2 | 3 | 1 | 1 |
| | | ● | ● | | 4 | 5 | 2 |
| No treat zone | — | | | 0 | 0 | 0 | 0 |

In the actual field test, the growth regulator of the invention was shown to have high inhibitory effects for ear emergence. No chemical injury to bent grasses was observed.

Test Example 5

In a Manilagrass (*Zoysia matrella*) turf where southern crabgrasses (*Digitaria ciliaris* Koel.) were grown, a test zone of 1 m×1 m was provided. Benzyladenine (Beanine for painting; made by Rikengreen; containing 1% benzyladenine) and ethephon (Ethrel 10 soluble concentrate; Nissan Chemical Industries; containing 10% ethephon) were diluted in a predetermined amount of water. The respectively diluted solutions were applied to each test zone at the first application (Day 0) at a dose as indicated in Table, and after a lapse of 17 days the second application was carried out. The first application was conducted before the ear emergence of southern crabgrasses (*Digitaria ciliaris* Koel.). The amount of solution scattered was 150 mL/m² both in the first and second applications. The inhibitory effect for the ear emergence of southern crabgrasses (*Digitaria ciliaris* Koel.) within the area of 1 m×1 m was evaluated according to the standard as described in Table 7. Table 8 shows the results. The symbol "●" in Table 8 indicates the treatment with each agent, and "–" means untreated. Dose means the amount at a single application.

As seen above, the growth regulator of the invention also exhibited a high inhibitory effect for the ear emergence of southern crabgrasses (*Digitaria ciliaris* Koel.). No chemical injury to Manilagrass (*Zoysia matrella*) was observed.

Industrial Applicability

The growth regulator and the growth-regulating kit for gramineous weeds according to the present invention are preferable for treatment of gramineous weeds growing in turf.

What is claimed is:

1. A growth regulator for gramineous weed(s) that is a synergistic combination of ingredients comprising at least one cytokinin; and at least one ethylene-producing substance.

2. The growth regulator for gramineous weed(s) as claimed in claim 1, wherein the cytokinin is benzyladenine.

3. The growth regulator for gramineous weed(s) as claimed in claim 1, wherein the ethylene-producing substance is ethephon.

4. The growth regulator for gramineous weed(s) as claimed in claim 1, wherein the gramineous weed(s) are those belonging to the genus *Poa* or *Digitaria*.

5. The growth regulator for gramineous weed(s) as claimed in claim 1, wherein the gramineous weed(s) is annual bluegrass (*Poa annua* L.) or southern crabgrass (*Digitaria ciliaris* Koel.).

6. A kit for regulating the growth of gramineous weed(s), comprising a synergistic combination of ingredients comprising a first agent containing cytokinin and a second agent containing an ethylene-producing substance.

7. The kit for regulating the growth of gramineous weed(s) as claimed in claim 6, wherein the cytokinin is benzyladenine.

8. The kit for regulating the growth of gramineous weed(s) as claimed in claim 6, wherein the ethylene-producing substance is ethephon.

9. The kit for regulating the growth of gramineous weed(s) as claimed in claim 6, which is formulated for application to a gramineous weed(s) belonging to the genus *Poa* or *Digitaria*.

10. The kit for regulating the growth of gramineous weed(s) as claimed in claim 6 which is formulated for application to a gramineous weed(s) that is annual bluegrass (*Poa annua* L.) or southern crabgrass (*Digitaria ciliaris* Koel.).

11. A method for regulating the growth of gramineous weed(s), comprising contacting a gramineous weed(s) with the plant growth regulator as claimed in claim 1.

12. A method for regulating the growth of gramineous weed(s) in turf, comprising contacting a gramineous weed(s) in turf with the plant growth regulator as claimed in claim 1.

13. A method for regulating the growth of gramineous weed(s), comprising contacting a gramineous weed(s) with a synergistic combination of ingredients comprising a cytokinin and an ethylene producing substance, wherein said cytokinin and ethylene-producing substance are contacted with the gramineous weed(s) at the same time or at different times.

14. The method for regulating the growth of gramineous weed(s) as claimed in claim 13, wherein the cytokinin and ethylene-producing substances are contacted with gramineous weed(s) growing in turf.

15. The method of claim 13, wherein the gramineous weed(s) comprise annual bluegrass (*Poa annua* L.).

16. The method of claim 13, wherein the gramineous weed(s) comprise southern crabgrass (*Digitaria ciliaris* Koel.).

17. The method of claim 13, wherein the turf comprises at least one lawn grass selected from the group consisting of a Japanese lawn grass, summer western lawn grass, and a cool temperature lawn grass.

18. The method of claim 13, wherein the cytokinin is applied before ear emergence of the gramineous weed(s).

19. The method of claim 13, wherein the at least one cytokinin is applied in a dose ranging from 0.5mg to 16 mg per 1 $m^2$ of application area and the at least one ethylene-producing substance is applied in an amount ranging from 20 mg to 320 mg per 1 $m^2$ of application area.

20. The method of claim 19, wherein the at least one cytokinin is benzyladenine and the at least one ethylene-producing substance is ethephon and these compounds are applied in combination.

\* \* \* \* \*